United States Patent [19]

Kishioka

[11] Patent Number: 4,900,481
[45] Date of Patent: Feb. 13, 1990

[54] OZONIC BUBBLE WATER GENERATOR

[76] Inventor: Takashi Kishioka, 5-7-9,, Teraikedai, Tondabayashi-shi, Osaka, Japan

[21] Appl. No.: 261,930

[22] Filed: Oct. 25, 1988

[30] Foreign Application Priority Data

Oct. 29, 1987 [JP] Japan .............................. 62-165769[U]

[51] Int. Cl.$^4$ ............................................... B01F 3/04
[52] U.S. Cl. ..................................... 261/64.4; 261/76; 261/DIG. 22; 261/DIG. 42
[58] Field of Search ................ 261/DIG. 42, DIG. 22, 261/76, 64.4

[56] References Cited

U.S. PATENT DOCUMENTS

| | | | |
|---|---|---|---|
| 1,090,044 | 3/1914 | Fuss | 261/DIG. 42 |
| 2,056,663 | 10/1936 | Foulke | 261/DIG. 42 |
| 2,316,832 | 4/1943 | Aghnides | 261/DIG. 22 |
| 2,388,753 | 11/1945 | Mallmann et al. | 261/DIG. 42 |
| 2,754,097 | 7/1956 | Hjulian | 261/DIG. 22 |
| 2,778,800 | 1/1957 | Sheahan | 261/DIG. 42 |
| 3,362,697 | 1/1968 | Silva et al. | 261/DIG. 42 |
| 3,843,521 | 10/1974 | Zeff | 261/DIG. 42 |
| 4,049,552 | 9/1977 | Arff | 261/DIG. 42 |
| 4,382,044 | 5/1983 | Baumgartner et al. | 261/DIG. 42 |

FOREIGN PATENT DOCUMENTS 2137208 2/1973 Fed. Rep. of Germany ... 261/DIG. 42
776115 1/1935 France ........................ 261/DIG. 42

Primary Examiner—Tim Miles
Attorney, Agent, or Firm—Oblon, Spivak, McClelland, Maier & Neustadt

[57] ABSTRACT

According to the present invention, a decompression chamber is provided in a water flow pipe and an ozonizer chamber of an ozonizer part is integrally connected with the water flow pipe to communicate with the decompression chamber, to thereby define a body. Thus, an apparatus is compactly finished while operation for assembling the apparatus is simplified. A check valve is provided between the decompression chamber and the ozonizer chamber to prevent water in the decompression chamber from flowing into the ozonizer chamber upon stoppage of water-supply to the inlet. Thus, counterflow of the water in the decompression chamber into the ozonizer chamber is prevented, so that danger of an electric shock is reduced, to thereby ensure safety.

3 Claims, 5 Drawing Sheets

OZONIC BUBBLE WATER GENERATOR

BACKGROUND OF THE INVENTION

1. Field of the Invention

The present invention relates to an ozonic bubble water generator which generates ozonic bubble water.

2. Description of the Prior Art

In the field of medical industry, food industry or the like, highly bactericidal ozonic bubble water is frequently employed for washing hands. In a conventional ozonic bubble water generator for generating such ozonic bubble water, an ozonizer part for generating ozone and a water flow pipe for mixing the generated ozone with water are separately and independently assembled into the generator. Consequently, assembling operation is complicated and the ozonic bubble water generator thus assembled is increased in size, to restrict the service space.

SUMMARY OF THE INVENTION

The present invention is directed to an ozonic bubble water generator which generates ozonic bubble water by mixing ozone into water.

According to the present invention, an ozonic bubble water generator comprises: (a) a body provided with (a-1) a water flow pipe having an inlet for receiving water, an outlet for discharging ozonic bubble water, a small diameter part defined between the inlet and the outlet and a decompression chamber provided in an outlet side of the small diameter part, and (a-2) an ozonizer part having an ozonizer chamber integrally connected with the water flow pipe to communicate with the decompression chamber and an ozonizer electrode pair provided in the ozonizer chamber so that ozone generated in the ozonizer chamber is attracted into the decompression chamber by a venturi effect caused upon flow of the water from the small diameter part into the decompression chamber; and (b) a check valve provided between the decompression chamber and the ozonizer chamber to prevent the water in the decompression chamber from flowing into the ozonizer chamber upon storage of water-supply to the inlet.

Accordingly, an object of the present invention is to provide a compact ozonic bubble water generator, whose assembling operation is simplified.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
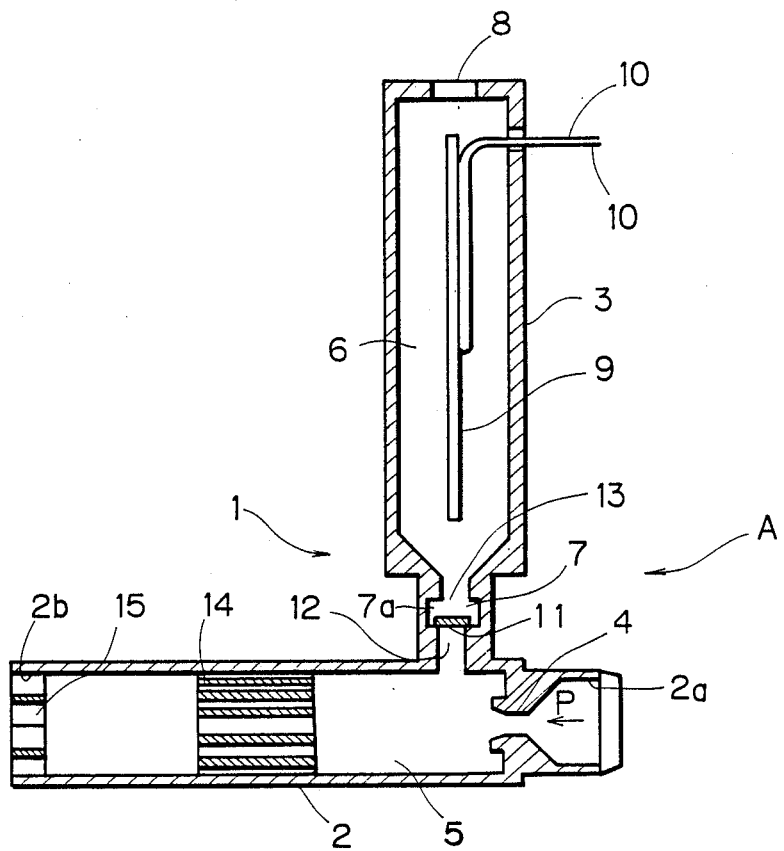
FIG. 1 is a sectional view showing an ozonic bubble water generator according to an embodiment of the present invention.

FIG. 1 is a sectional view showing an ozonic bubble water generator A according to an embodiment of the present invention. As shown in FIG. 1, a body 1 of vinyl chloride is formed of a water flow pipe 2 and a substantially tubular ozonizer part 3 which is integrally connected to the outer peripheral portion of the water flow pipe 2. There are an inlet 2a for receiving water and an outlet 2b for discharging ozonic bubble water which is generated by the ozonic bubble water generator A on both ends of the water flow pipe 2. A water flow path provided in the water flow pipe 2 is partially finished in a small diameter to define a small diameter part 4, while a decompression chamber 5 is provided in an outlet side of the small diameter part 4.

On the other hand, an ozonizer chamber 6 is provided in the ozonizer part 3 so as to communicate with the decompression chamber 5 through a communicating portion 7.

An air inlet hole 8 for introducing air is formed in an end of the ozonizer part 3 which is opposite to the communicating portion 7, while an ozonizer electrode pair 9 of ceramic is provided in the ozonizer chamber 6. High frequency voltage is applied to the ozonizer electrode pair 9 from a power supplier (not shown) provided in the exterior of the ozonizer part 3 through wires 10, to thereby generate ozone through electric discharge caused across the ozonizer electrode pair 9. In the ozonic bubble water generator A, water is injected into the water flow pipe 2 from the inlet 2a to flow along an arrow P, whereby pressure in the decompression chamber 5 is reduced by a venturi effect based on the small diameter part 4 and then ozone generated in the ozonizer chamber 6 is sucked into the decompression chamber 5 through the communicating portion 7.

Figure 2:
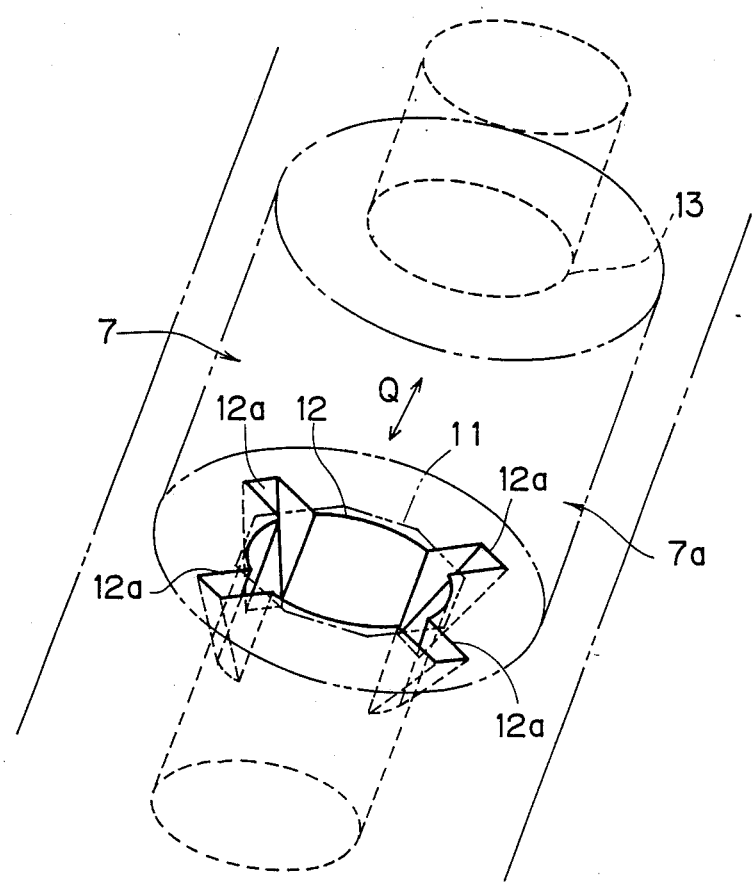
FIG. 2 is a perspective view schematically showing the structure of a communicating portion of the embodiment shown in FIG. 1.

FIG. 2 is an enlarged perspective view schematically showing the structure of the communicating portion 7. As shown in FIG. 1 or 2, a check valve receiving chamber 7a having a large diameter is provided in the communicating portion 7. A check valve 11 of fluoro rubber, which is in the form of a regular octagon, is provided in the check valve receiving chamber 7a to be slidable along an arrow Q. A water flow pipe side opening 12 of the check valve receiving chamber 7a is finished to be smaller in diameter than the check valve 11, and inclined ozone passage grooves 12a, which are tapered toward the water flow pipe 2, are provided in four portions of its peripheral edge of the check valve receiving chamber 7a. An ozone side opening 13 of the check valve receiving chamber 7a is also finished to be smaller in diameter than the check valve 11. When water flows in the flow pipe 2 along the arrow P, the check valve 11 is attracted by negative pressure of the decompression chamber 5 to be in contact with the peripheral edge of the water flow pipe side opening 12, so that ozone currently generated in the ozonizer chamber 6 is guided to the decompression chamber 5 through the inclined ozone passage grooves 12a. If the outlet 2b of the water flow pipe 2 is erroneously blocked during such flow of the water, the check valve 11 is pushed up with the water in the check valve receiving chamber 7a to block the ozone side opening 13, to thereby prevent the water contained in the decompression chamber 5 from infiltration into the ozonizer chamber 6 through the communicating portion 7.

Figure 3A:
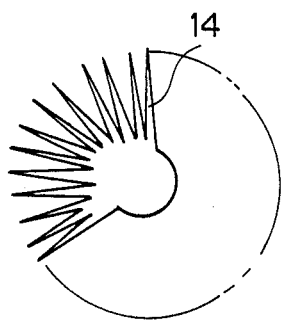
FIGS. 3A and 3B are front elevational views showing resistance plates, respectively.
Figure 4:
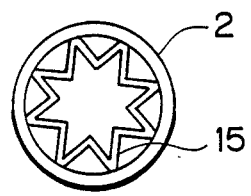
FIG. 4 is a front elevational view showing a uniflux plate.

On the other hand, the water flow pipe 2 is provided with a resistance plate 14 in an outlet side of the decompression chamber 5. As shown in FIG. 3A, the resistance plate 14 is formed by alternately folding a thin plate member and circularly shaping the same, to regulate the water flow in the water flow pipe 2 and stir the same in the decompression chamber 5, to thereby efficiently mix ozone guided into the decompression chamber 5 with the water for generating ozonic bubble water. A uniflux plate 15 is provided in the outlet 2b of the water flow pipe 2. The uniflux plate 15, which is formed by radially shaping a thin member as shown in FIG. 4, is engagedly fixed to the inner peripheral surface of the water flow pipe 2, to prevent circumferential dissipation of ozonic bubbles when the ozonic bubble water is discharged from the outlet 2b of the water flow pipe 2.

In the ozonic bubble water generator A, water is injected into the water flow pipe 2 from the inlet 2a to flow along the arrow P, while high frequency voltage is applied to the ozonizer electrode pair 9 of the ozonizer part 3 so that ozone is generated by electric discharge caused in the ozonizer chamber 6. The ozone thus generated is guided to the decompression chamber 5 through the inclined ozone passage grooves 12a of the communicating portion 7 by a venturi effect based on the small diameter part 4. The ozone thus guided to the decompression chamber 5 is mixed with the water stirred by the resistance plate 14 to generate ozonic bubble water, which is discharged from the outlet 2b while being prevented from circumferential dissipation of ozonic bubbles by the uniflux plate 15.

When the outlet 2b is blocked by some cause such as a prank during discharge of the ozonic bubble water, the water flow is restricted, to thereby cause undesired flow of the water from the decompression chamber 5 into the ozonizer chamber 6. In such case, however, the check valve 11 blocks the ozone side opening 13, to prevent infiltration of the water into the ozonizer chamber 6 as hereinabove described, whereby the water is not brought into contact with the ozonizer electrode pair 9 of high voltage. Thus, the water defines no energization path which may cause an electrical shock, to thereby sufficiently ensure safety.

The ozonic bubble water generator A according to the present invention can be compactly finished since the water flow pipe 2 is integrally connected with the ozonizer part 3 to form the body 1 as hereinabove described, while operation for assembling the same is extremely simplified since the wires 10 may be simply connected to a power supply part (not shown) and the inlet 2a of the water flow pipe 2 may be connected to a water supply pipe. Further, dissipation of ozonic bubbles is prevented due to employment of the uniflux plate 15 so that the ozonic bubble water sufficiently contains ozonic bubbles to cause soft feeling.

Figure 3B:
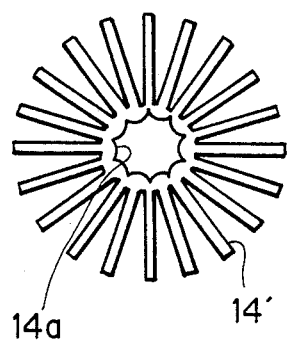

Although the resistance plate 14 is prepared by alternately circumferentially folding a thin plate member as shown in FIG. 3A in the above embodiment, another resistance plate 14' may be prepared by radially arranging a plurality of plate-shaped members from a through hole 14a as shown in FIG. 3B. Further, although the ozonizer part 3 and the water flow pipe 2 are arranged perpendicularly to each other in the above embodiment, these elements are not restricted to such relation. The water flow pipe 2 may be bent halfway.

Figure 5:
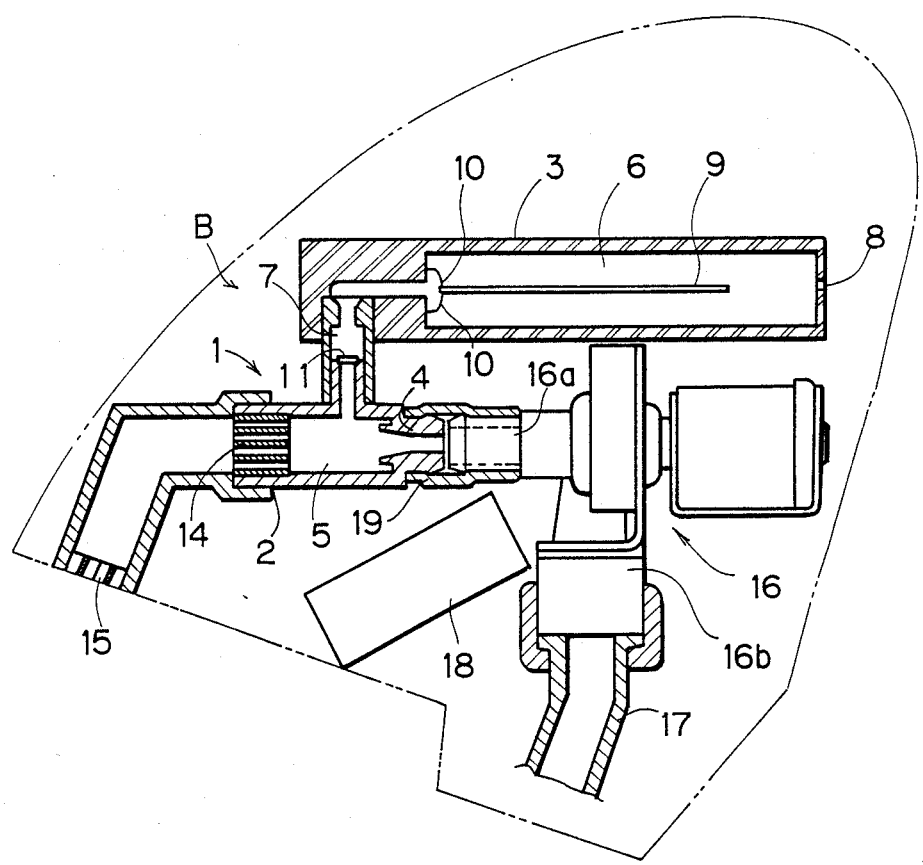
FIG. 5 is a sectional view showing an ozonic bubble water system, into which the inventive ozonic bubble water generator is integrated.

FIG. 5 is a sectional view showing an ozonic bubble water generating system, into which an ozonic bubble water generator B according to the present invention is integrated. In the ozonic bubble water generator B shown in FIG. 5, a portion of a water flow pipe 2 close to an outlet 2b is downwardly bent, while an upper part of a communicating portion 7 is bent so that an ozonizer part 3 is arranged in parallel with the water flow pipe 2, dissimilarly to the ozonic bubble water generator A shown in FIG. 1. Other structure of this generator is similar to that of the ozonic bubble water generator A shown in FIG. 1. In this ozonic bubble water generating system, an inlet 2a of the water flow pipe 2 of the ozonic bubble water generator B is connected with a discharge opening 16a of an electromagnetic valve 16 by a connecting pipe 19, while a suction port 16b of the electromagnetic valve 16 is connected to a water-supply pipe 17. A diffuse reflection type infrared sensor 18 is provided under the water flow pipe 2, to determine whether or not a user is washing his hands.

Figure 6:
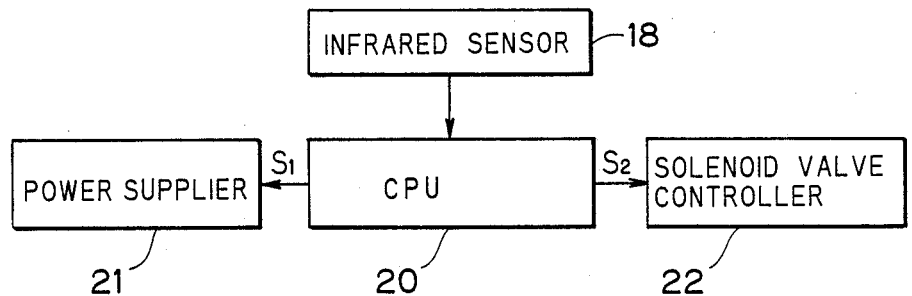
FIG. 6 is a block diagram showing a control system for the ozonic bubble water system shown in FIG. 5.

FIG. 6 is a block diagram showing a control system for controlling the ozonic bubble water generating system of FIG. 5. As shown in FIG. 6, the infrared sensor 18 is connected to a CPU 20, which creates an ozonizer control signal $S_1$ for the ozonizer part 3 and a switch control signal $S_2$ for the electromagnetic valve 16 on the basis of a signal from the infrared sensor 18, and then the signals $S_1$ and $S_2$ are supplied to a power supplier 21 and an electromagnetic valve controller 22, respectively. The power supplier 21 supplies high frequency voltage to an ozonizer electrode pair 9 of the ozonizer part 3 on the basis of the ozonizer control signal $S_1$, to thereby generate ozone in the ozonizer chamber 6. The electromagnetic valve controller 22 opens/closes the electromagnetic valve 16 on the basis of the switch control signal $S_2$, to control supply/stop of water to the water flow pipe 2.

When the user holds out his hands under the outlet 2b of the ozonic bubble water generating system to wash his hands, the infrared sensor 18 detects such action so that the ozonizer part 3 is driven by a command from the CPU 20 to generate ozone, while the electromagnetic valve 16 is opened to inject water into the water flow pipe 2, to thereby generate and discharge ozonic bubble water. When the infrared sensor 18 detects that the user puts back his hands to stop washing, on the other hand, operation of the ozonizer part 3 is stopped by a command from the CPU 20, while the electromagnetic valve 16 is simultaneously closed to stop discharge of the ozonic bubble water.

According to this ozonic bubble water generating system, ozonic bubble water is automatically discharged when the user holds out his hands, while such discharge is automatically stopped when the user puts back his hands. Thus, the user can wash his hands without touching the system, whereby a sanitary effect is further improved. Further, since the ozonizer part 3 is arranged in parallel along the water flow pipe 2, the service space is effectively utilized to reduce the size of the system.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An ozonic bubble water generator for generating ozonic bubble water by mixing ozone into water, said generator comprising:
   (a) a body being provided with:
   (a-1) a water flow pipe having an inlet for receiving said water, an outlet for discharging said ozonic bubble water, a small diameter part defined between said inlet and said outlet and a decompression chamber provided in an outlet side of said small diameter part, and
   (a-2) an ozonizer part having an ozonizer chamber integrally connected with said water flow pipe to communicate with said decompression chamber and an ozonizer electrode pair provided in said ozonizer chamber, ozone generated in said ozonizer chamber being attracted into said decompression chamber by a venturi effect caused upon flow of said water from said small diameter part into said decompression chamber; and
   (b) a check valve provided between said decompression chamber and said ozonizer chamber for preventing said water in said decompression chamber from flowing into said ozonizer chamber upon stoppage of water-supply to said inlet, said check valve having an outlet connected to said decompression chamber, the outlet having passage grooves connected thereto so that ozone flows to said decompression chamber when the outlet is blocked.

2. An ozonic bubble water generator in accordance with claim 1, wherein
   a resistance plate for stirring said ozonic bubble water is provided in an outlet side of said decompression chamber.

3. An ozonic bubble water generator in accordance with claim 1 or 2, wherein
   a uniflux plate for preventing dissipation of ozonic bubbles is provided in the vicinity of said outlet.

* * * * *

UNITED STATES PATENT AND TRADEMARK OFFICE
CERTIFICATE OF CORRECTION

PATENT NO. : 4,900,481

DATED : FEBRUARY 13, 1990

INVENTOR(S) : TAKASHI KISHIOKA

It is certified that error appears in the above-identified patent and that said Letters Patent is hereby corrected as shown below:

TITLE PAGE:

The number of drawings sheets is incorrect, should read:

--4 Drawing Sheets--.

Signed and Sealed this

Second Day of July, 1991

Attest:

HARRY F. MANBECK, JR.

*Attesting Officer*     *Commissioner of Patents and Trademarks*